United States Patent [19]

Sugino

[11] Patent Number: 5,765,551
[45] Date of Patent: Jun. 16, 1998

[54] PORTABLE FACE SHIELD FOR PERFORMING ARTIFICIAL RESPIRATION

[76] Inventor: Kazuo Sugino, Genjo, 6-12, Omiya Chome, Osaka, Japan

[21] Appl. No.: 651,214

[22] Filed: May 22, 1996

[51] Int. Cl.[6] .................................................. A61M 16/00
[52] U.S. Cl. ........................... 128/203.11; 128/202.28; 128/202.29
[58] Field of Search ..................... 128/202.28, 202.29, 128/203.11

[56] References Cited

U.S. PATENT DOCUMENTS

| | | | |
|---|---|---|---|
| 3,626,936 | 12/1971 | Barker | 128/203.11 |
| 4,819,627 | 4/1989 | Connors | 128/203.11 |
| 4,819,628 | 4/1989 | Eisenberg et al. | 128/203.11 |
| 4,858,605 | 8/1989 | Levy | 128/203.11 |
| 4,909,245 | 3/1990 | Wollenhaupt | 128/203.11 |
| 5,088,485 | 2/1992 | Schock | 128/203.11 |
| 5,119,809 | 6/1992 | Gerson | 128/203.11 |
| 5,127,397 | 7/1992 | Kohnke | 128/203.11 |
| 5,355,877 | 10/1994 | Cheng | 128/203.11 |
| 5,386,822 | 2/1995 | Jones | 128/203.11 |
| 5,437,269 | 8/1995 | Gooch | 128/203.11 |
| 5,511,543 | 4/1996 | Shirley | 128/203.11 |
| 5,562,093 | 10/1996 | Gerson | 128/203.11 |

*Primary Examiner*—Aaron J. Lewis
*Attorney, Agent, or Firm*—Alfred E. Miller

[57] ABSTRACT

A shielded artificial respiratory device that functions as a one-way ventilator of exhalation and which can be easily folded into a small package that can be stored in a wallet or purse. The device has soft sheets thermally bonded and placed around a patient's mouth and valve on the underside of the sheets for inserting in the patient's mouth. The valve has an expandable internal pouch and a spaced exterior cover with a ventilator provided therebetween.

11 Claims, 5 Drawing Sheets

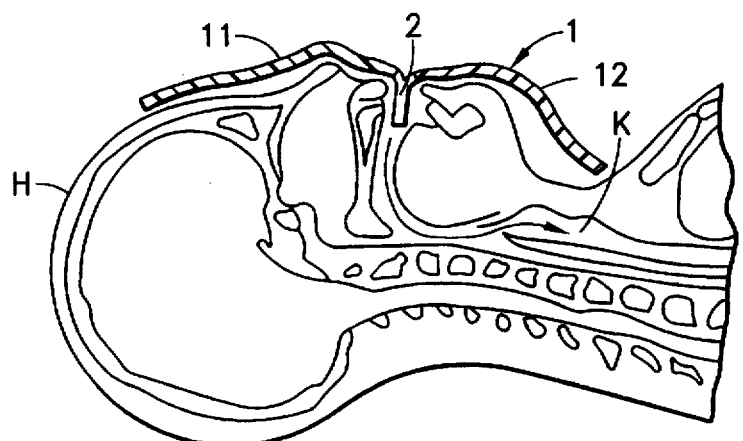
FIG.5
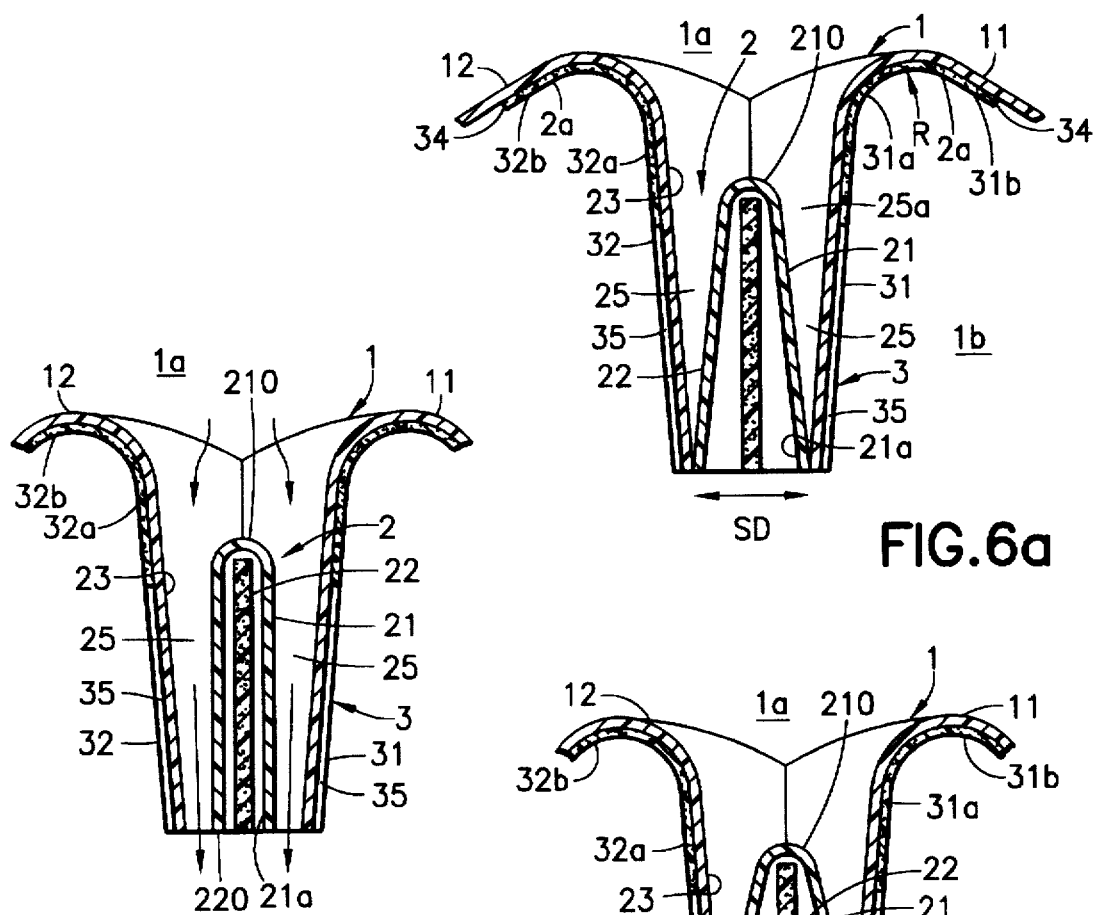
FIG.6a
FIG.6b
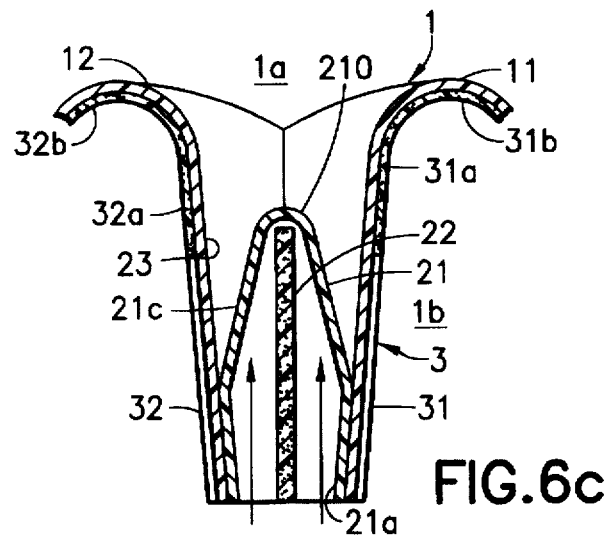
FIG.6c

PORTABLE FACE SHIELD FOR PERFORMING ARTIFICIAL RESPIRATION

The present invention relates to a device for performing life saving mouth-to-mouth respiration without the operator directly touching the mouth of the patient.

BACKGROUND OF THE INVENTION

It is well known that cardio-pulmonary resuscitation is one of the most effective first aid methods for reviving a person who is unconscious, who has stopped breathing or whose heart has stopped, or a combination of these conditions. In cardio-pulmonary resuscitation a rescuer, such as a medic, first lifts the chin of the patient in order to open the respiratory tract of the patient from the mouth to the lungs. The rescuer then closes the nostrils of the patient and puts his or her mouth to the patient's mouth and blows breath directly into the respiratory tract of the patient without air escaping to the atmosphere. At the same time the rescuer gives a heart massage by applying pressure to the patient's chest.

A problem arises from utilizing the above procedure since mouth-to-mouth respiration requires the rescuer to directly touch the mouth of the patient. Consequently, there is a possibility of an infection or disease being transmitted from the patient to the rescuer. This problem is presently becoming extremely serious due to the fact that the patient may be stricken with the acquired immune deficiency syndrome, known as AIDS. This is especially true when the patient is suspected of being a drug user or a homosexual.

DESCRIPTION OF THE PRIOR ART

Some mouth-to-mouth respirators have been fabricated in the form of a soft sheet in the center of which is an exhalation flow valve which permits breath to be blown through the mouth of the patient. In this construction the sheet is opened and placed around the mouth of the patient with the exhalation flow valve being inserted in the mouth of the patient and through this valve the exhalation of the rescuer is blown directly into the respiratory tract of the patient, as seen in Japanese Patent Publication No. 5-64074 corresponding to U.S. patent application Ser. No. 76,949 filed Jul. 23, 1987. The exhalation valve is made of a hard material, such as hard resin and works as a ventilator for the exhalation of the rescuer to the patient. Since the exhalation flow valve is very hard and bulky, even when folded, it cannot be carried in a wallet or a purse.

It is a feature of the present invention to provide a portable respirator which functions as a one-way ventilator for exhalation, but which is not bulky when folded and is truly portable and capable of being carried in a wallet or purse.

Another aspect of the present invention is to provide a sanitary device for effectively performing mouth-to-mouth resuscitation.

A further feature of the present invention is to fabricate a respirator device that has all soft material, such as a soft sheet cover, a thin valve and a pouch made of a soft sheet.

A further aspect of the present invention is to provide a pouch in the respirator which captures the exhalation of the patient and prevents it from following a path to the rescuer's mouth.

Other features and advantages of the invention will be apparent from the following description of the preferred embodiment and from the claims.

BRIEF DESCRIPTION OF THE DRAWINGS

FIG. 2 is an enlarged cross-section view taken along the line A—A of FIG. 1a.

FIG. 3 is an enlarged cross-section view taken along the lines B—B of FIG. 1 a.

FIG. 5 shows the respirator device inserted in the mouth of a patient.

FIGS. 6(a), (b) and (c) are cross-sectional views showing the valve functions during the utilization of the present respirator device with a patient.

DESCRIPTION OF THE PREFERRED EMBODIMENTS

Figure 1A:
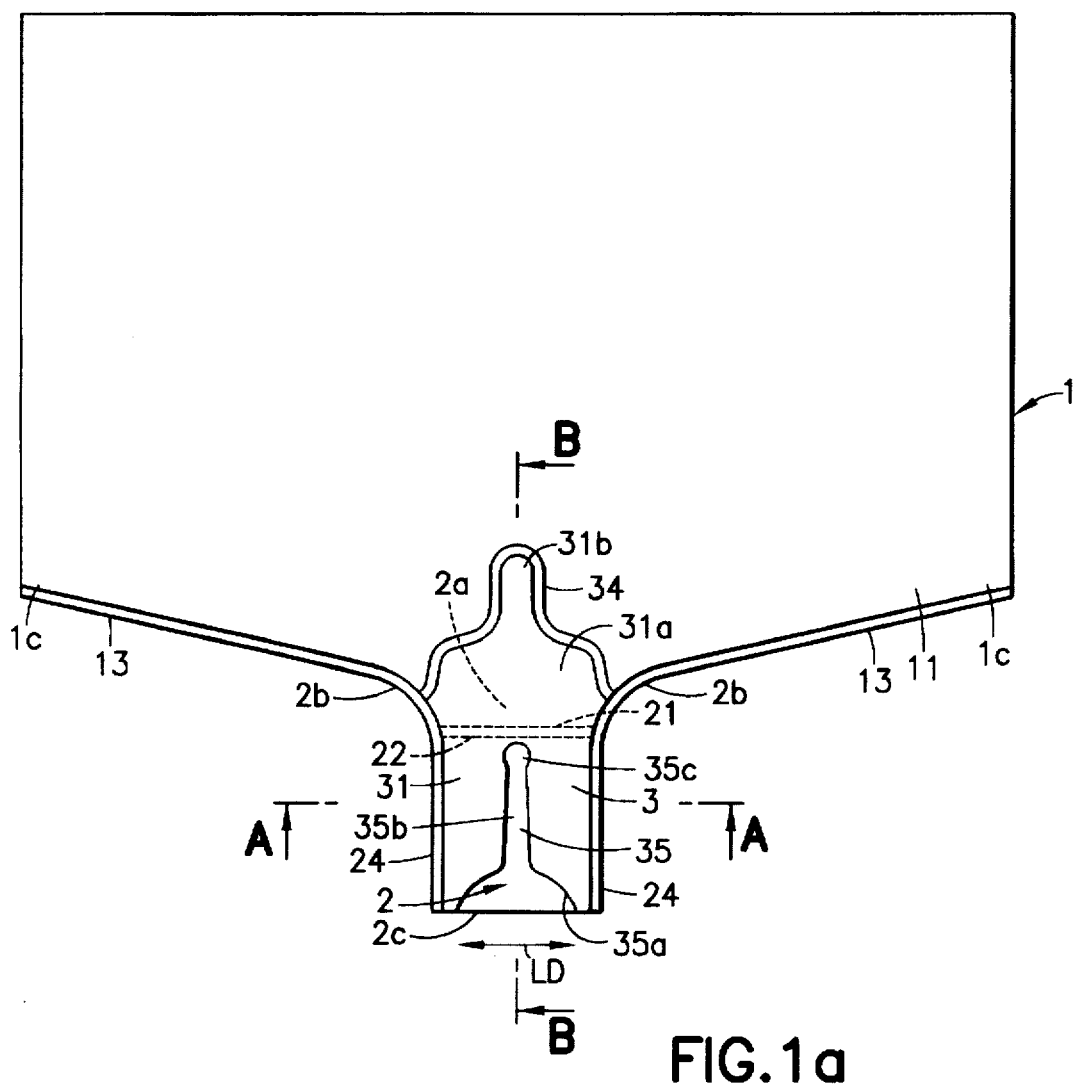
FIG. 1a is a top plan view of the respirator device constructed and arranged according to the teachings of the present invention.
Figure 1B:
FIG. 1b is a front elevational view thereof.
Figure 1C:
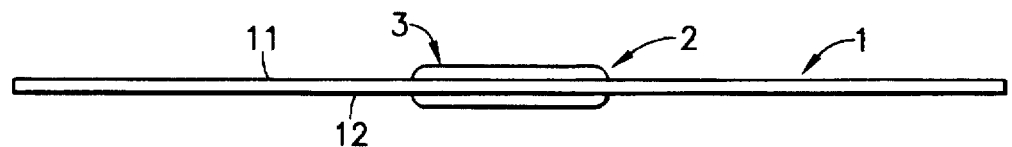
FIG. 1c is a rear elevational view thereof.
Figure 1D:
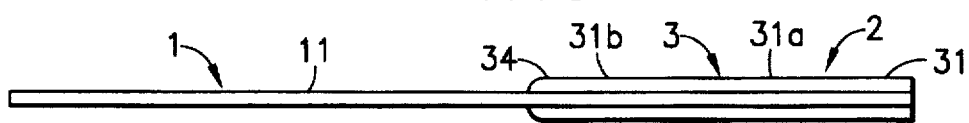
FIG. 1d is an elevational view taken from the left side thereof.
Figure 2:
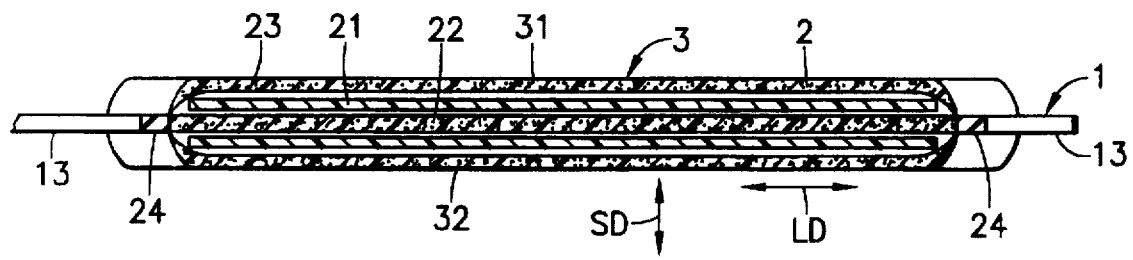

The respirator device constructed in accordance with the teachings of the present invention constitutes a cover, referred to generally by the numeral 1, having sheets 11 and 12 of soft polymerized material that is to be placed along the patient's mouth as seen in FIG. 5 of the drawings. On the reverse side of the cover 1 is a long, relatively thin valve 2 that is inserted in the patient's mouth. The valve 2 is provided with a valve cover 3, as seen in FIGS. 1c, 2 and 6a. The soft sheets 11 and 12 are best thermally bonded together at 13, as seen in FIG. 4.

The valve 2, as seen in FIGS. 2 and 3, and FIGS. 6a, 6b and 6c includes a pouch 21, which is fabricated from two pieces of soft sheet which is connected together to form a pouch having a flat sponge 22 inserted therein. An exterior cover 23 covers the pouch 21 as it is projected from the soft sheets 11 and 12 of the cover 1, as seen in FIGS. 2 and 6a. As seen in FIG. 1a and FIG. 2 the bonded part 24, the sponge 22 and the exterior cover 23 are bonded together to form the valve 2 which has a long, thin cross-section, as particularly seen in FIG. 2.

Figure 4:
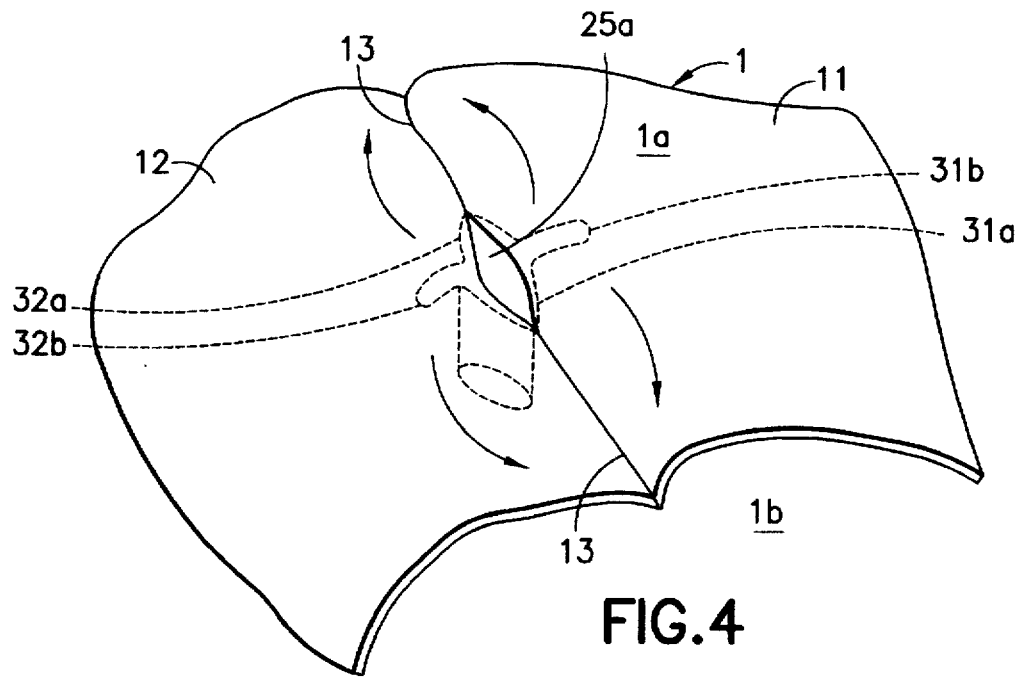
FIG. 4 is a perspective of the respirator device which is open for use.

In order to use the present respirator device, the sheets 11 and 12 of the cover 1 are opened to the full extent as seen in FIG. 4, and the valve 2 is inserted in the patient's mouth. The cover 1 is placed around the mouth of the patient H as seen in FIG. 5. Referring to FIGS. 4 and 5, the upper side of the cover 1 becomes the surface side 1a to the rescuer, and the reverse side 1b has the projecting valve 2.

Figure 3:
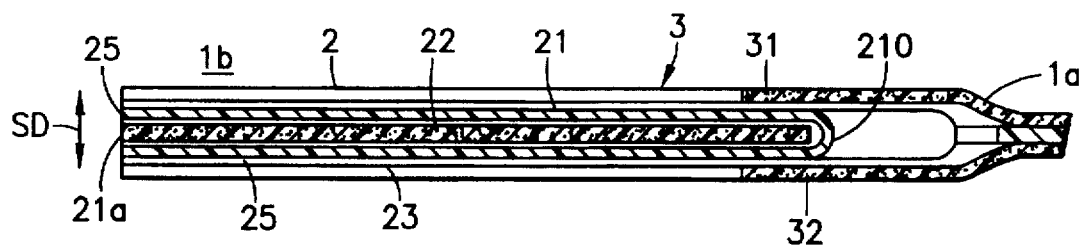

As seen in FIGS. 3 and 6a, the pouch 21 has a closed edge 210 on the surface side 1a of the cover. The other edge 220, as seen in FIG. 6b, on the reverse side 16 of the cover, is open. It should be noted that between the pouch 21 and the exterior cover 23 an opening exists forming a ventilator 25 from the surface side 1a of the cover 1 through the reverse side 1b of the cover 1.

Referring now to FIG. 2 and 3, the valve holder 3 is made of two pieces 31 and 32 of sheet material that is harder than the soft sheets 11 and 12 described above and are bonded together at 24, as seen in FIGS. 1a and 2, and cover the valve 2 from both sides. As seen in FIGS. 4 and 6, the sheets 31 and 32 comprise holder bases 31a and 32a, which project from the bonded part 24 to the to the cover 1, and the long thin holder pieces 31b and 32b project from the center of the holder bases 31a and 32b. Sheet 31 is heat bonded to sheet 11 which forms the cover 1 by it's outer edges 34 of the holder base 31 and the holder base 31a and the holder piece 31b, and the other sheet 32 is also heat bonded to sheet 11 which forms the cover 1 by it's outer edge 34 of the holder base 32a and the holder piece 32b.

When the cover is inserted on the face of a patient and opened, as seen in FIG. 4, the holder bases 31a and 32a and holder pieces 31b and 32b are curved and widely opened in opposite directions to each other forming a big curvature R, as seen in FIG. 6a, and holds the open mouth area of the cover, which is closely located to the root part 2a opposite to the line of the minor axis SD of the valve 2. The result is the expansion of the opening 25a to the surface of the cover of the ventilator 25 in valve 2.

As seen in FIGS. 1a and 6b, each of the sheets 31 and 32 of the valve holder 3 has a cut out 35 that has a shape which extends into the root part 2a of the valve 2 from edge 2c of the valve, which is the open edge. The cutout 35 is formed with an enlarged part 35a, and opening into a canal 35b which narrows to a closed end part 35c which prevents the sheets 31 and 32 from being caught in the canal part 35b.

When the cover 1, as seen in FIG. 1a, is folded along the line 13 that contains the root part 2b of the major axis LD of the valve 2, the line 13 forms a rising shape opposite to the valve 2 from the root part 2b of the valve 2 to the edge 1c of the cover 1.

When performing mouth-to-mouth respiration using the above-mentioned respirator, the rescuer first lays back the head of the patient H, as seen in FIG. 5, and slightly raises the jaw. This procedure opens the respiratory tract K for air to go from the mouth of the rescuer to the lungs of the patient. The valve 2 is then inserted into the mouth of the patient while adjusting the major axis of the valve 2 to the right-left direction of the mouth. The two pieces of sheet material are unfolded and placed around the mouth of the patient H. Since the valve 2 is covered with valve holder 3 which is somewhat hard, the insertion of the valve is easier to insert in the patient's mouth.

Figure 7:
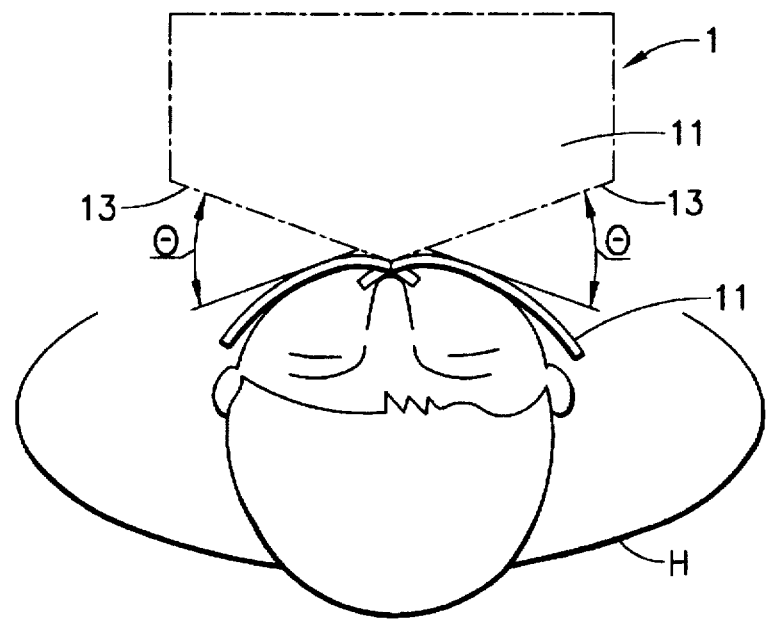
FIG. 7 is a top plan view showing the respirator device functioning in the mouth of a patient.

Since cover 1 is folded on the line representing the bonded part 13 in FIG. 1a which has an elevated v-shape opposite to the valve 2 from the root part 2b of the major axis LD of the valve 2 to the edge of the cover 1c, the angle θ of the edge of the cover 1c in FIG. 7 becomes greater when the cover is opened and placed around the mouth of the patient H than when the bonded part 13 is placed on a level plane. As seen in FIG. 4, in this way the edge of the cover 1c pulls the center and widens the opening 25a on the surface side of the cover 1a of the ventilator 25. Thus, when the cover is placed on a patient the surface side 1a of the ventilator opens automatically. This enables the rescuer to place his or her mouth on the opening 25a and immediately blow the exhalation in the patient's mouth, and enables the exhalation to flow smoothly into the respiratory tract K of the patient H. At the same time the rescuer directly pinches the nose of the patient to close the nostrils without pinching the cover 1.

The valve 2, which is inserted in the mouth of the patient H is shown in greater detail in FIG. 6a. Since the pouch 21 is closed at one end of the edge 210 on the surface side to the rescuer 1a, the exhalation the rescuer blows into the valve 2 goes through and expands the ventilator area 25 between the pouch 21 and the exterior cover 23, and flows through the ventilator into the respiratory tract K of the patient H, as clearly seen in FIG. 6b. In order to lessen the work of the rescuer in blowing the exhalation the cut-out 35 enables the valve holder 3 to expand out as the ventilator 25 expands.

Figure 10:
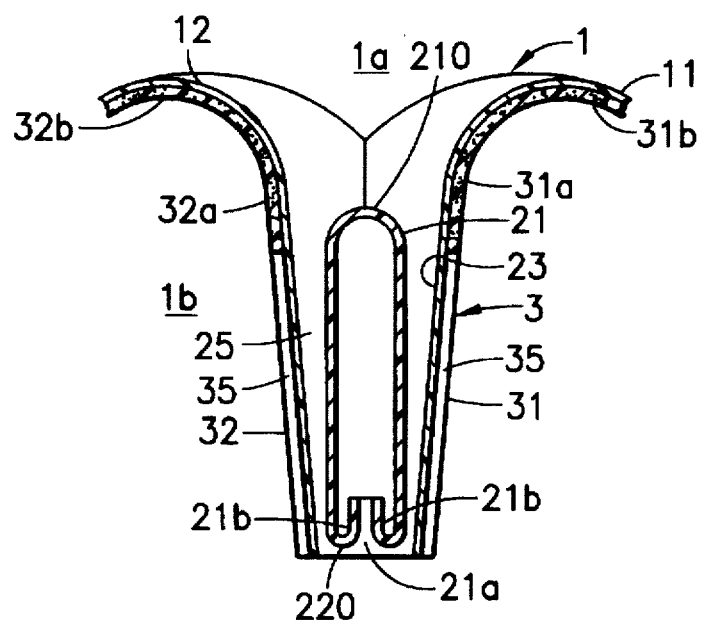
FIG. 10 is a cross-section view of another embodiment of the present invention.

Referring now to FIG. 6c, the exhalation which comes from the patient H enters into the opening part 21a of the other edge 220, As seen in FIG. 10 which opens because the pouch 21 and the exterior cover 23 are both fabricated of a soft sheet material. The ventilator 25 is closed by pouch 21 made from a soft material which is adhered to the exterior cover 23, and consequently the exhalation of the patient H flows into the pouch 21 of which the edge on the surface side is closed, thus preventing the exhalation from flowing back to the rescuer.

It should be evident that even though the valve 2 is constructed of a soft sheet and a sponge, the valve functions as a one way valve, as seen in FIG. 6a. Moreover, the breath from the patient H flows precisely into the pouch 21 since the opening part 21a is always maintained in an open position because of the sponge 22 inserted in the pouch 2.

The present respirator device is flat and soft comprising a cover 1, two pieces of soft sheet 11 and 12, a valve 2 which includes a flat sponge 22, a soft sheet pouch 21, an exterior cover 23, a valve holder 3 which is constructed of somewhat harder sheets 31 and 32. Therefore, the present respirator device can be folded into a small package which can be stored in a wallet or purse, and can be put into use immediately in case of an emergency.

Figure 8:
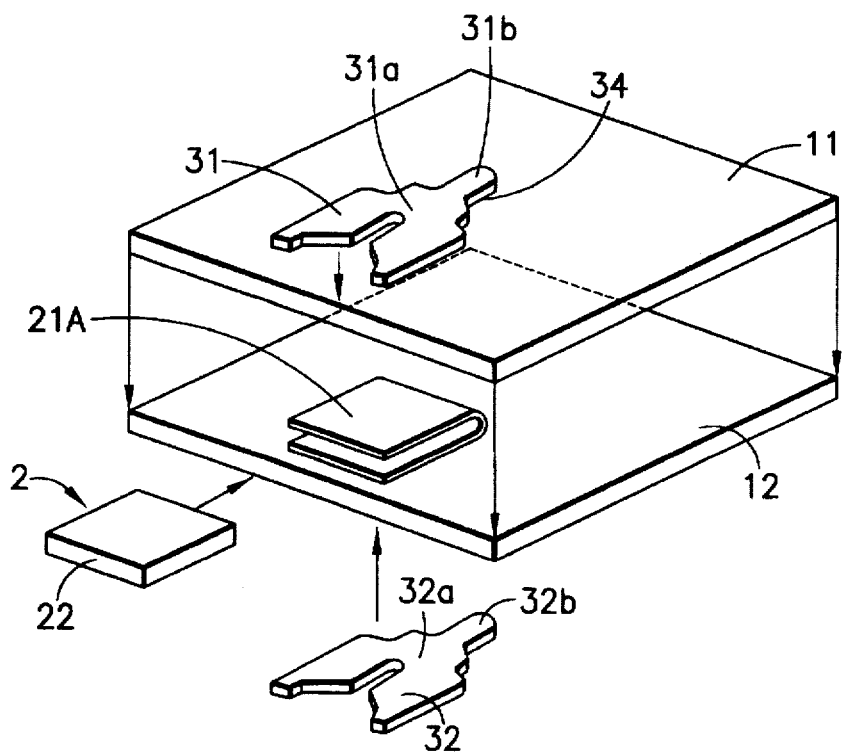
FIGS. 8 and 9 are diagrammatic illustrations of the process for making a respirator device according to the teachings of the present invention.
Figure 9:
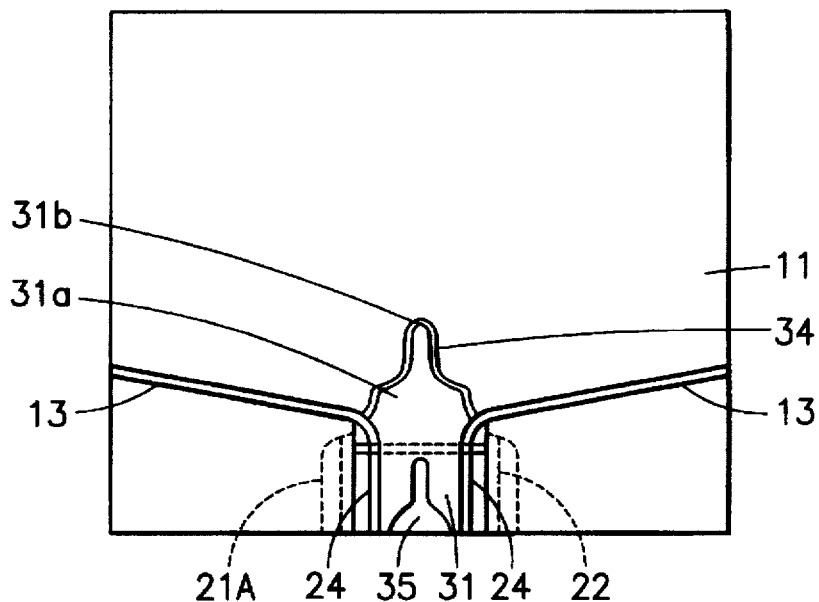

A method of manufacturing the present respirator device is seen in FIG. 8 in which the sheets 31 and 32 which are somewhat hard are cut out, and the holder bases 31a and 32a are formed along with holder pieces 31b and 32b and cut-out 35. The sheets 31 and 32 are placed on the valve 2 and attached to the outer side of the sheets 11 and 12 of the cover 1, and thereafter bonded alongside their outer edge 34 by heat bonding. The sponge 22 is placed in the soft sheet 21A which is folded in two. Hard sheets 31 and 32 are thermally bonded to the soft sheets 11 and 12 as well as sheet 21A and the sponge 22 together alongside of the bonded parts 13 and 24 of FIG. 9. Finally, the outer edge of the bonded parts 13 and 14 is cut and the respirator of FIG. 1 is constructed. At this stage, the above-described folded sheet 21A forms the pouch 21.

It is preferred to use air tight sheets, such as chloroethylene or polyethylene for soft sheets 11, 12 and 21A, the sponge 22, and the harder sheets 31 and 32. Hard chloroethylene or soft but thicker chloroethylene can be used for sheets 31 and 32 than the materials used for sheets 11 and 12.

Another embodiment of the present invention is seen in FIG. 10. The respirator device shown does not use a sponge 22 as seen in the previous embodiment, but instead the device incorporates cuffs 21b that projects from the edge 220 of the reverse side of the cover 1b of the pouch 21. Each of these cuffs 21b do not stick together, and thus forms the opening 21a between the cuffs. At the same time, the restitutive force of the cuffs works to draw the major side 21c (FIG. 6c) which is opposite to the minor axis SD of the pouch 21, close to the side of the exterior cover 23. When the rescuer blows exhalation in, the pressure of the exhalation bends the pouch 21 which makes each side touch each other and opens the ventilator 25. When the exhalation from the patient comes out, it flows into the pouch 21 through the opening 21a thus expanding the pouch. Consequently this respirator device works effectively for the purposes intended.

Although the valve holder 3 covers the whole valve with the exception of cut-out 35, the valve holder 3 may also only cover the root part 2a since its purpose is to support the root part 2a of the minor axis of the valve 2. In fact the valve holder can be omitted altogether. In that case the respiration procedure is performed by widening the center of the opened sheet with the rescuer's fingers, maintaining the opening 25a of the ventilator 25. The pouch 21 can also be fabricated with one of the edges 210 on two pieces of sheet bonded together by thermal adhesion.

While the present invention has been described and shown with reference to preferred embodiments, it is not intended to be limited by the present disclosure but should cover equivalents in accordance with the spirit and scope of the invention as defined in the following claims.

What I claim is:

1. A shielded artificial respirator device for use by a rescuer on a patient comprising a first interior cover fabricated of a soft sheet material that is placed around a patient's mouth, and being provided with a substantially centrally located opening exposing a patient's mouth, a relatively long, thin one way valve secured to the back of said first cover and inserted in a patient's mouth, said valve having an inverted pouch including an inner wall and an outer wall of soft material with the open end being remote from said first cover, a second exterior cover bonded to said first cover, the first and second cover having a space therebetween and said valve being located within said covers, and when said portion of said covers and adjacent valve are inserted in a patient's mouth for artificial respiration by a rescuer, air exhaled under pressure by a rescuer enters said space between said covers and the adjacent valve and flows into a patient's respiratory tract, and upon exhalation of air by such a patient air flows through the open end of said pouch causing expansion of said pouch whereby the outer wall of said pouch engages the inner wall.

2. The device as claimed in claim 1 wherein said cover is comprised of two flat pieces comprised of two flat pieces that are thermally bonded together along adjacent marginal edges of each sheet.

3. The device as claimed in claim 1 wherein said pouch is provided with a flat sponge which functions to maintain said open end in an open position.

4. The device as claimed in claim 1 wherein the open end of said pouch is provided with a cuff at the bottom edge of said pouch forming said open end.

5. The device as claimed in claim 1 wherein said respirator device is provided with a valve holder which covers at least the root part of said valve, and said valve holder being fabricated of a harder sheet material than the soft sheet material of said valve.

6. The device as claimed in claim 5 wherein the valve holder is fabricated of polyethylene material.

7. The device as claimed in claim 5 wherein the valve holder is fabricated of soft but thicker chloroethylene than the chloroethylene material used in said soft sheet cover.

8. The device as claimed in claim 1 wherein said soft sheet cover is fabricated of chloroethylene material.

9. The device as claimed in claim 1 wherein said soft sheet cover is fabricated of polyethylene material.

10. The device as claimed in claim 5 further comprising a cut-out canal for said valve holder having an enlarged opening port connected to said canal, and a closed narrower end part of said canal for preventing said sheet from being caught in said canal upon the use of said device.

11. A shielded artificial respirator device for use by a rescuer on a patient comprising a first interior cover fabricated of soft sheet material that is placed around a patient's mouth and being provided with a substantially centrally located opening exposing a patient's mouth, a relatively long thin one way valve secured to a back of said first cover and inserted in a patient's mouth, said valve having an inverted pouch including inner and outer walls of soft material including at least one open end being remote from said first cover, a second exterior cover having an inner wall and being attached to said first cover, the first and second covers having a space therebetween and when said valve is inserted in a patient's mouth for artificial respiration by a rescuer air exhaled under pressure by a rescuer enters said space between said pouch and the exterior cover and flows into a patient's respiratory tract, and upon exhalation of air by such a patient air flow through the open end of said pouch causing expansion of said pouch whereby the outer wall of said pouch engages the inner wall of said exterior cover.

* * * * *